United States Patent [19]
Johnson

[11] 4,175,525
[45] Nov. 27, 1979

[54] FUEL VAPORIZER SYSTEM FOR INTERNAL COMBUSTION ENGINES

[75] Inventor: Edward E. Johnson, Richardson, Tex.

[73] Assignee: Auto-Miser International Manufacturing Corp., Fort Worth, Tex.

[21] Appl. No.: 785,750

[22] Filed: Apr. 8, 1977

[51] Int. Cl.[2] ........................ F02P 5/04; A61M 15/00
[52] U.S. Cl. .................................... 123/134; 123/136; 261/18 A
[58] Field of Search ................. 123/134, 119 B, 25 L, 123/136, 133; 261/23 A, 18 A, 124, 70

[56] References Cited

U.S. PATENT DOCUMENTS

| | | | |
|---|---|---|---|
| 2,625,142 | 6/1953 | Chambers | 261/18 A |
| 3,540,423 | 11/1970 | Tolles | 123/136 |
| 3,749,376 | 7/1973 | Alm et al. | 123/134 |
| 3,762,385 | 10/1973 | Hollnagel | 123/119 B |
| 3,805,755 | 4/1974 | Miles | 123/119 B |
| 3,961,616 | 6/1976 | Brown | 123/119 B |
| 3,973,534 | 8/1976 | Amos | 123/119 B |
| 4,000,727 | 1/1977 | Walker | 123/136 |
| 4,031,869 | 6/1977 | Onishi et al. | 123/136 |
| 4,051,205 | 9/1977 | Grant | 261/70 |

*Primary Examiner*—Charles J. Myhre
*Assistant Examiner*—R. A. Nelli
*Attorney, Agent, or Firm*—Jack A. Kanz

[57] ABSTRACT

Disclosed is a system for injecting a mixture of vaporized fuel and air into the intake manifold of an internal combustion engine downstream from the carburetor throttle valve. The system includes a sealed vaporizer operationally parallel with the conventional carburetor system. The vaporizer includes a stabilized float valve for controlling fuel flow therethrough and various check valve arrangements and component arrangements which eliminate any possibility of lost fuel in case of collision or upset of a vehicle powered by an engine employing the vaporizer system.

7 Claims, 1 Drawing Figure

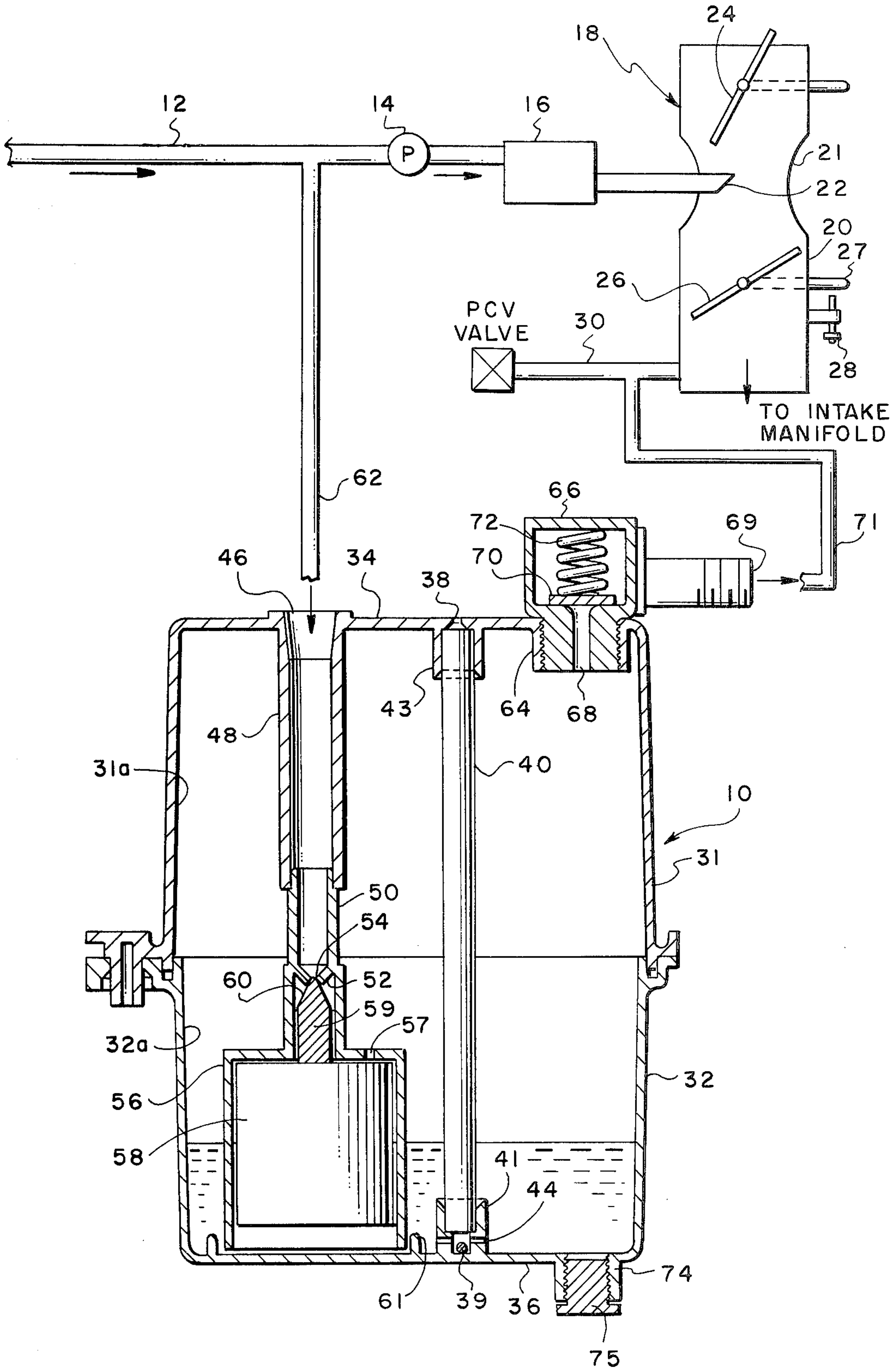
24
18
12
14
P
16
21
22
20
27
26
PCV VALVE
30
28
TO INTAKE MANIFOLD
62
66
72
69
71
70
46
34
38
43
64
68
48
40
31a
10
31
50
54
60
52
59
57
32a
56
32
58
41
44
61
39
36
74
75

FUEL VAPORIZER SYSTEM FOR INTERNAL COMBUSTION ENGINES

This invention relates to carburetion systems for spark ignition internal combustion engines. More particularly, it relates to apparatus for injecting a mixture of vaporized fuel and air into the intake manifold of an internal combustion engine at a point between the carburetor and the distribution ports in the manifold.

Conventional spark ignition internal combustion engines employ an air and fuel mixing and distribution system comprising a carburetor for mixing air and fuel and an intake manifold for distributing the mixture to the combustion cylinders. A combustible fuel and air mixture is formed in the carburetor by drawing air through a venturi where fuel is drawn into and mixed with the air. It is well known that the fuel and air mixture formed in conventional carburetors, however, is not the ideal mixture since the fuel is sprayed into the air stream in the form of a mist or small droplets. It is also well known that the efficiency of an internal combustion engine, i.e., the amount of work produced in terms of fuel consumed, is partially dependent upon the degree to which the fuel is dispersed in the air. Therefore, if the fuel is completely vaporized prior to injection into the combustion chamber of the engine, combustion thereof is more complete, thus resulting in higher efficiency. Furthermore, more complete combustion of the fuel lowers the concentration of hydrocarbon (HC) and carbon monoxide (CO) emissions from the engine.

In view of the scarcity and ever-increasing cost of hydrocarbon fuels and federal regulations governing permissible emissions from internal combustion engines used in automobiles and the like, various systems have been devised which attempt to lower emissions and/or increase efficiency in internal combustion engines. Techniques for lowering emissions have been primarily directed to systems such as catalytic converters and air injector reactor systems and the like for removing toxic or otherwise undesirable emissions from the exhaust. Such systems produce no useful work and therefore do not increase efficiency. On the contrary, such systems as the air injector reactor systems require an air pump which is driven by the engine, thus further lowering the amount of useful work available from the engine.

In some modern engines attempts have been made to lower the emission of nitrogen oxides by introducing exhaust gas into the intake manifold, thereby lowering combustion temperatures and lowering the concentration of nitrogen oxides formed. However, introduction of an essentially inert gas into the intake manifold detrimentally affects the power output of the engine, thus lowering fuel efficiency. Thus, most conventional techniques for lowering emissions reduce the efficiency of the engine and thus, while lowering emissions, detrimentally affect fuel economy and available power.

In accordance with the present invention, a fuel vaporization system is provided which operates in parallel with a conventional carburetor system to inject a mixture of vaporized fuel and air directly into the intake manifold downstream from the carburetor. The fuel vaporizer system of the invention provides a mixture in which fuel is completely vaporized, thereby assuring more complete combustion of fuel which, in turn, promotes better fuel economy and lowers undesirable hydrocarbon and carbon monoxide emissions. The apparatus may be readily installed on conventional internal combustion engines without major modification of the conventional fuel supply system and, in accordance with the invention, can be made completely fail-safe and collision proof so as to eliminate any additional fire or escaped fuel hazards in the event of a collision or upset of the automobile. Furthermore, the apparatus can be made from readily available materials and is extremely simple in design, thus permitting easy and ready fabrication and installation thereof.

Other features and advantages of the invention will become more readily understood when taken in connection with the appended claims and attached drawings in which the sole FIGURE is a partially schematic and partially sectional view of the preferred embodiment of the invention.

As illustrated in the drawing, the vaporization system comprises a fuel vaporizer unit generally indicated at 10 connected between the fuel supply line 12 and the intake manifold of an internal combustion engine operationally parallel with the carburetor. For illustrative purposes the conventional fuel distribution system of an internal combustion engine is illustrated schematically comprising a fuel line 12 for conducting fuel from a fuel tank (not shown) through a pump 14 into a float valve controlled reservoir 16 in carburetor generally indicated at 18. As schematically illustrated the carburetor 18 comprises a barrel 20 with a venturi 21 therein. The exit end of barrel 20 is attached to the intake manifold. Fuel is drawn into the venturi through jet 22. The conventional carburetor usually includes a choke valve 24 upstream from the jet 22 and a throttle valve 26 downstream from jet 22. Engine speed is normally controlled by throttle valve 26 which is linked to a throttle control means by lever 27. Normally, the minimum closure of throttle valve 26 is controlled by an idle adjustment means illustrated in simple form by an idle adjustment screw 28.

To control crankcase emission resulting from blowby and the like, modern internal combustion engines employ a positive crankcase ventilation (PVC) system. In essence the PVC system comprises a conduit 30 connected between the crankcase and the intake manifold at a point downstream from the throttle valve so that vapors are drawn from the crankcase through the conduit into the intake manifold. To maintain the desired pressure differential between the crankcase and the intake manifold and to prevent gas from entering the crankcase in case of backfiring, etc., the vent through which the crankcase communicates with the conduit is controlled by a normally closed spring loaded check valve commonly known as a PCV valve.

The fuel vaporizer unit 10 of the invention comprises a cylindrical cannister comprised of two mating halves. The top half 31 and the bottom half 32 are joined to form an enclosure having a top wall 34 and a bottom wall 36. The top half 31 and bottom half 32 thus define a sealed enclosure 10 having a top wall 34 and a bottom wall 36 joined by side walls **31*a* and 32*a***.

As illustrated in the drawing, top wall 34 is provided with an aperture 38 which acts as an air inlet means. Air inlet means 38 communicates with an air conduit 40 which depends internally from the top wall 34 and, in the preferred embodiment, terminates in an upstanding boss 41 on the inner surface of bottom wall 36. Conduit 40 may be formed as an integral part of top wall 34 or secured within a downwardly depending boss 43 as shown. In any event, conduit 40 should provide leakproof means for conducting air which enters through air inlet 38 to a point near the bottom wall 36 of the enclosure.

In the preferred embodiment conduit 40 terminates in upstanding boss 41 which is provided with a plurality of apertures 44 near the base thereof so that air conducted through air conduit 40 exits the conduit by way of apertures 44 well below the level of any liquid contained within the enclosure 10. Since apertures 44 are below the liquid fuel level in the enclosure, fuel vapor may not exit the enclosure by way of the air inlet 38. If desired, air inlet 38 may be provided with a suitable filter (not shown) or the like to prevent foreign matter from entering the enclosure.

Vaporizer unit 10 is provided with a fuel inlet 46 which communicates with an internally downwardly depending fuel conduit 48. In preferred embodiment fuel conduit 48 is integrally formed as a part of top wall 34 and extends a substantial distance within the enclosure. Conduit 48 mates with a nipple 50 which forms a continuous extension of conduit 48. In the embodiment illustrated, nipple 50 contains an integrally formed disc 52 having a tapered aperture 54 therein which defines a valve seat. A cylindrical cage 56 depends from nipple 50 below the valve seat 54. The lower end of cage 56 is open and extends to a point near the bottom wall 36. A cylindrical float 58 is contained therein. Centrally positioned on the top surface of float 58 is a upwardly extending shaft 59 which terminates in an upwardly extending needle 60. Needle 60 is adapted to mate with the valve seat 54 and thereby obstruct passage of fluid through valve seat 54 in either direction when the needle is positioned within the valve seat 54. In the embodiment illustrated the cage 56 terminates slightly above the bottom wall 36 so that fluid may pass through the cage to the bottom wall 36 and between the cage and the bottom wall. Upstanding bosses 61 extending from the bottom wall 36 may be used to assure lateral stability of the cage.

In the embodiment illustrated cage 56 is a cylindrical housing closed at its upper end and open at its lower end. The float 58 is a buoyant cylindrical body with external dimensions which conform to the internal dimension of the cage except that the cage may have a longer axial length. Therefore, float 58 may move freely with the cage 56 along its vertical axis only.

As will be more fully described hereinbelow, in normal operation the container 10 contains a volume of liquid fuel. Air entering air inlet 38 is drawn through apertures 44 and bubbled through the liquid to entrain fuel vapor in the air. Bubbling air through the liquid fuel and vibration of the container 10 because of engine and vehicular vibration cause turbulent agitation of the liquid contained in the vaporizer unit. In order to assure that needle 60 is properly aligned with the valve seat 54 at all times and to further assure that the needle remains fully seated in the valve seat when the desired liquid level is attained in the container, the float 58 must be substantially immune to agitation of the liquid. If the float 58 is not protected from the agitating liquid, the valve will not be properly closed and liquid fuel will be admitted into the container in excess of the desired amounts. To protect the float from agitation yet permit the float 58 to react to the liquid level in the container, float 58 is constrained by the cage 56. In the preferred embodiment, the open end of cage 56 terminates approximately 0.030 inch from the bottom wall 36. In this manner the fluid level within the cage 56 will be the same as the fluid level outside the cage, but the liquid surface within the cage upon which the float 58 is carried is protected from the agitation caused by bubbling air through the liquid. To further damp fluctuations in fluid level, upstanding boss 61 is provided on the floor of the vaporizer unit. Boss 61 is circular in plan view, completely surrounds the open end of the cage 56, is spaced horizontally approximately 0.125 inch from the cage and extends above the open end of the cage. Thus air bubbles cannot enter the cage.

Float 58 floats freely within the cage with no restriction to its movement along its vertical axis. However, cage 56 prevents any lateral movement which would mis-align needle 60 and seat 54. It will be observed that liquid entering the container flows through valve seat 54 and over the float within the cage 56, thus assuring that the flow of liquid is always essentially in the outward direction under the cage. Since the cage is enclosed on its top end, air trapped above the float would prevent the float from rising with the liquid level. Accordingly, a vent 57 is provided in the top of cage 56 to permit air to enter and exit from the space above float 58 as required. The vent 57 is relatively small, however, thus controlling the rate at which float 58 may move along its vertical axis and thereby damping vertical movement of the float without restricting the distance of its vertical travel.

Fuel inlet 46 communicates with fuel supply line 12 by means of conduit 62 as schematically illustrated. It will thus be realized that fuel entering fuel conduit 48 by means of conduit 62 and inlet 46 exits conduit 48 through valve seat 54. The fuel then flows downwardly through cage 56 to the bottom wall 36. As the liquid fuel level in the unit 10 rises, float 58 will be buoyed upwardly until such time as needle 60 mates with the valve seat 54. It will be readily understood that when the float valve is in the up position as illustrated, fuel flow into the enclosure 10 is stopped. However, when the level of liquid fuel is lowered, the float likewise is lowered, thus opening valve seat 54 and permitting additional fuel to enter the enclosure. The float valve thus regulates the level of liquid fuel in the enclosure 10 to maintain a predetermined desired level of fuel in the enclosure 10.

An outlet 64 is provided in top wall 34 to permit vaporized fuel and air to be withdrawn from the vaporizer unit 10. As illustrated in the drawing outlet 64 is provided with a check valve 66. In the preferred embodiment check valve 66 comprises a housing with an inlet 68 and outlet 69. Inlet 68 threadedly engages outlet 64 to form a sealed connection therewith and provide fluid communication between the interior of vaporizer unit 10 and the interior of the check valve housing 66. Inlet 68 is blocked by a resilient disc 70 which is held in place by coil spring 72. It will thus be observed that disc 70 totally obstructs the inlet 68 to prevent the flow of any fluid into the vaporizer unit 10 by way of check valve 66 but allows fluid flow in the opposite direction when the pressure differential across disc 70 is sufficient to overcome spring 72. Outlet 69 is connected to the intake manifold downstream from the throttle valve 26 by conduit 71. This connection may be conveniently made by connecting conduit 71 with the PCV conduit 30 between the PCV valve and the intake manifold. Thus the vaporized fuel and air mixture will be diluted with warm air drawn from the crankcase and injected directly into the intake manifold. Mixing the vapor with warm air insures that the vapors will be further diluted and will not coalesce to form unwanted droplets.

If desired, vaporizor unit 10 may be provided with a drain outlet 72 which is closed by plug 75.

In the preferred embodiment the fuel inlet conduit 62 is connected to fuel line 12 between the fuel tank and the fuel pump 14 as illustrated in the drawing. Accordingly, fuel is not pumped into the container 10 by the fuel pump. Instead, fuel is drawn into the container 10 by the reduced pressure therein caused by the vacuum in the intake manifold. Fuel is initially drawn into the cannister 10 in an amount sufficient to cause float 58 to rise until needle 60 blocks valve seat 54. With valve seat 54 blocked by the needle 60, further flow of fuel into the cannister 10 is stopped and, because of the reduced pressure in cannister 10, air is drawn into air inlet 38 and conducted to the bottom of the container by way of conduit 40. The air exits conduit 40 by apertures 44 and thus is bubbled through the liquid fuel to vaporize the fuel and fill the container 10 with a mixture of air and fuel vapor. It should be noted, however, that the fuel is in the form of vapor, not a mist or droplets. The air and fuel vapor mixture is withdrawn from the top of the container through check valve 66 and conducted into the intake manifold by way of conduits 71 and 30.

As the fuel is vaporized and withdrawn from the vaporizer 10 float 58 is lowered and the fuel supply in the vaporizer replenished until the float again rises and needle 60 again blocks valve seat 54. In this manner, a predetermined desired level of liquid fuel is maintained in the vaporizer unit 10 at all times and a mixture of vaporized fuel and air contained in the vaporizer 10 above the liquid fuel.

It will be noted that the fuel vaporizer unit operationally parallels carburetor 18 and injects vaporized fuel into the intake manifold downstream from the throttle valve 26. Accordingly, the fuel vapor and air mixture may be drawn into the intake manifold when throttle valve 26 is closed. Therefore, adjustment of the idle screw 28 may be necessary to obtain the desired idle speed of an engine equipped with the vaporizer system of the invention. Also the fuel and air mixture provided by the carburetor must be adjusted to provide an appropriately lean mixture since additional fuel is being introduced downstream from the carburetor venturi.

In the preferred embodiment, the container 10 is formed from mating halves 31 and 32 hermetically sealed by tongue and groove connections as illustrated. Accordingly, when the container 10 is assembled, the tongue and groove connection is hermetically sealed and permanently joined to form an enclosed container approximately 4.175 inches in diameter and 4.750 inches high. The container 10 is permanently sealed to form a totally leak-proof container which is tamper-proof and maintains the internal parts in a permanent relationship. Float 58 is allowed approximately 0.03 inches of travel between the full open and closed positions, thus permitting a maximum of approximately three ounces of liquid fuel in the container. Approximately 16.7 cubic inches of vaporized fuel and air may be maintained within the container above the liquid.

The tension of spring 72 in check valve 66 must be sufficient to maintain the check valve closed until the desired pressure differential thereacross is developed. In the preferred embodiment, spring 72 maintains the check valve closed until a vacuum of one and one-half inches of mercury is developed in check valve housing 66. It will thus be observed that until a vacuum of one and one-half inches of mercury is developed, the conventional carburetion system operates in the conventional manner. However, when a vacuum in excess of one and one-half inches is obtained, check valve 66 opens and permits vaporized fuel and air to be drawn from the vaporizer 10 directly into the intake manifold.

The required operating pressure differential of check valve 66 provides an essential safety feature of the invention. It will be observed that the float 58 closes valve seat 54 when approximately three ounces of liquid fuel is in the container 10. Therefore, the maximum amount of liquid in the container at any time is approximately three ounces. In the event the automobile in which the vaporization unit of the invention is employed is involved in a collision or upset and the vaporizer unit 10 inverted, the three ounces of liquid fuel in the container cannot develop sufficient hydrostatic pressure to open check valve 66. Accordingly, all the fuel in the vaporizer 10 is contained within the vaporizer and cannot escape to cause a lost fuel hazard. It should also be noted that fuel conduit 40 and nipple 50 form a closed conduit which extends from inlet 46 to valve seat 54 and that valve seat 54 is spaced a substantial distance from the side walls and from the top wall 34. Accordingly, in case of upset in which the vaporizer unit 10 is inverted and fuel conduit 62 ruptured, liquid fuel cannot escape from the vaporizer 10 by way of the fuel inlet 46 since the valve seat 54 is well above the liquid level of any fuel contained in the vaporizer unit. Furthermore, with only three ounces of liquid fuel in the container at any time, apertures 44 in the air inlet line will be above the level of the liquid in the container whenever the vaporization unit is in any position other than substantially upright. Therefore, since the vaporization unit is hermetically sealed, all possibility of escape of liquid fuel from the vaporizer is eliminated.

As an additional precaution to assure that no fuel may escape from the vaporizer system in case of an upset, the air inlet is also provided with an automatic closure means. In the preferred embodiment the air inlet 38 is conically flared outwardly on its internal face to provide a valve seat. A ball 39 which is smaller than the internal diameter of air conduit 40 but larger than air inlet 38 is placed in conduit 40. The ball 39 is more dense than the liquid fuel and thus sinks to the bottom of conduit 40 below apertures 44. Therefore, in normal operation the ball 39 does not affect flow through inlet 38 or apertures 44. However, if the vaporizer unit 10 is inverted, ball 39 rolls down conduit 40 by force of gravity and seats in the flared portion of air inlet 38, thus preventing the escape of gas or liquid through the air inlet. The ball 39 thus acts as a normally open check valve which automatically closes if the vaporizer is inverted.

It will be readily recognized that the dimensional characteristics of the vaporization system may vary within limits according to the size of the internal combustion engine with which it is employed. It has been discovered, however, that a vaporization unit of the dimensions described herein operates effectively when used in combination with internal combustion engines ordinarily used in automotive vehicles. To obtain the desired operational pressures and flow rates required to provide maximum effectiveness in combination with conventional automotive engines, the dimension hereinbelow have been found particularly suitable.

Using a cylindrical container with internal dimensions of approximately 4.175 inches in diameter by 4.70 inches high, nipple 50 and conduit 40 are joined to position valve seat 54 approximately 3½ inches from the top wall 34 and at least one inch from side wall 32*a*. An aperture of 0.03 inches with a 45° conical seat is provided in the integrally formed disc 52. Needle 60 is provided with a 30° from vertical slope on the point to assure effective closure and sealing of the valve.

The air inlet 38 is approximately 0.125 inch in diameter and is the limiting constriction in the air inlet means. Outlet 68 is approximately 0.250 inch in diameter and is the limiting constriction in the outlet line. The tension of spring 72 should be sufficient to maintain the check valve 66 closed until a pressure differential of one and one-half inches of mercury is developed thereacross. Therefore, an intake manifold vacuum of at least 1½ inches of mercury must be developed before the vaporization system is operational. These orifice sizes result in maintaining a vacuum of about 2½ inches of mercury in the container 10 when the manifold pressure is about 18 to 20 inches of mercury.

Under the conditions listed above, approximately three ounces of fuel will be drawn through the vaporization unit 10 from each gallon of fuel consumed. The remainder is drawn through the carburetor. However, since the fuel drawn through the vaporization unit is fully vaporized, the carburetor may be adjusted to produce a leaner mixture, resulting in more efficient combustion and cleaner burning of the fuel which substantially lowers hydrocarbon and carbon monoxide emissions. Furthermore, fuel economy is thereby promoted.

well as the internal components (except the float 58 and ball 39) and the check valve housing may be fabricated from injection molded nylon. This material is inert to gasoline, readily and inexpensively available, and readily forms gas-tight seals. A wall thickness of 0.070 inch is suitable for the container halves 31 and 32 which may be joined together by the tongue and groove arrangement illustrated by suitable fastening means and/or using a conventional O-ring or the like. Various other methods of forming a sealed container will be apparent to those skilled in the art.

In an effort to qualitatively determine the effects of the vaporization system of the invention under actual use conditions, a random sample was taken of 1975, 1976 and 1977 model automobiles, all currently in use. The exhaust gas emissions from each engine in the as-received condition were analyzed and the concentrations of hydrocarbons (HC) and carbon monoxide (CO) were noted. The fuel efficiency of each vehicle was also determined and noted using a standard dynamometer. Each engine was then equipped with the fuel vaporization system described hereinabove and the subjected to the identical tests. The only changes made to the automobiles between the first test and the second test was installation of the fuel vaporization system and appropriate adjustment of the carburetor mixture control. A tabulated comparison of the results obtained is presented in Table I.

TABLE I

| Vehicle | | | As Received | | | Equipped with Vaporizer System | | |
|---|---|---|---|---|---|---|---|---|
| Year | Make | Engine | ppm HC | % CO | MPG | ppm HC | % CO | MPG |
| 1976 | Monarch | V-8 302 | 400 | .5 | 20 | 250 | .25 | 23 |
| 1975 | GMC | V-8 455 | 225 | 1.0 | 14.5 | 0 | .2 | 17.5 |
| 1975 | Mustang | 4 cycle | 180 | 1.2 | 27 | 50 | 0 | 31 |
| 1977 | Cadillac | V-8 425 | 490 | .25 | 20.5 | 175 | .25 | 24 |
| 1976 | Thunderbird | V-8 460 | 500 | .75 | 11.5 | * | * | 16.5 |
| 1976 | Cordoba | V-8 360 | 275 | 4.0 | 18.5 | 110 | 1.0 | 22.5 |
| 1976 | Pacer | 6 cy. 250 | 150 | .18 | 19.5 | 20 | .02 | 22 |
| 1976 | Chevrolet | V-8 455 | 650 | 7.0 | ** | 300 | 4 | * |

*Unable to obtain stable test readings
**Not tested

Maximum efficiency of the vaporization system is obtained with a manifold pressure of about 18 to 20 inches of mercury is maintained.

It should be noted that the fuel conduit 62 providing fuel to the fuel inlet 46 is connected to the fuel supply conduit 12 between the fuel tank and the fuel pump 14. Thus fuel is not pumped into the vaporizer unit 10 by the fuel pump 14. Instead, fuel is drawn into the unit 10 by the reduced pressure in the intake manifold; thus fuel is admitted into the vaporizer only on an as-needed basis after the initial charge of approximately three ounces is admitted. Since the fuel must be drawn into the vaporizer as needed, the vaporizer system relies on neither gravity feed nor a fuel pump. Furthermore, the danger of over-filling by pumps or gravity flow is avoided and excess fuel cannot be pumped into or spilled from the vaporizer. Instead, the pressure in the vaporizer unit is maintained at a negative pressure of about two and one-half inches of mercury during operation and the pressure therein can never exceed atmospheric. By maintaining a negative pressure in the vaporizer, the fuel is more readily vaporized, thus aiding in vaporizing the liquid fuel as air is bubbled therethrough.

Since the vaporizer container and components need not withstand excessive pressure or temperatures, a wide range of materials is suitable for fabrication thereof. In the preferred embodiment, the enclosure, as As shown by the tabulated results, fuel efficiency was increased in every vehicle tested. Furthermore, significant hydrocarbon and CO emission reductions were obtained, particularly in those vehicles which exhibited high emissions in the as-received condition.

From the foregoing it will be readily observed that the system of the invention, when employed with internal combustion engines for vehicular use, significantly increases fuel efficiency while lowering exhaust emissions of hydrocarbons and CO. Furthermore, the system may be readily installed in conventional engines without major modification of the conventional air and fuel mixing systems; and offers no apparent detrimental effects to operation of the engine. In accordance with the teachings of the invention, the system is completely fail-safe and leak-proof, thereby presenting no additional hazards to operation of the engine and may be readily and inexpensively fabricated and installed using readily available and conventional equipment and materials.

While the invention has been described with particular reference to a specific embodiment thereof, it is to be understood that the form of the invention shown and described in detail is to be taken as the preferred embodiment of same, and that various changes and modifications may be resorted to without departing from the spirit and scope of the invention as defined by the appended claims.

What is claimed:

1. A fuel distribution system comprising:

(a) a carburetor including a throttle valve and connected to the intake manifold of an internal combustion engine;

(b) fuel supply means for supplying fuel to said carburetor including a fuel reservoir, a pump, a first fuel line connecting said reservoir and said pump and a second fuel line connecting said pump and said carburetor;

(c) conduit means connected between said intake manifold downstream from said throttle valve and a PCV valve;

(d) a fuel vaporizer having fuel inlet means, air inlet means and outlet means, said vaporizer comprising:

(i) a top wall, a bottom wall and side walls defining a sealed enclosure;

(ii) a fuel conduit depending internally from the top wall of said enclosure, the lower end of said fuel conduit containing an orifice defining a valve seat, said valve seat being positioned substantially equidistant from said top and bottom walls and a substantial distance from any side wall, the upper end of said fuel conduit communicating with said fuel inlet means;

(iii) float means supporting a needle valve aligned with and adapted for mating with said valve seat and preventing fuel flow therethrough when a predetermined fuel level is contained in the lower portion of said enclosure;

(iv) cage means affixed to said fuel conduit defining a housing coaxial with said valve seat surrounding the vertical sides of said float means and extending below said predetermined fuel level, thereby preventing lateral movement of said float means with respect to said valve seat and damping vertical movement of said float means;

(v) an upstanding boss extending from said bottom wall spaced from and completely surrounding the lower end of said cage means to prevent air bubbles from entering said cage means;

(vi) air conduit means for conducting air from said air inlet means to a point below said predetermined fuel level; and (vii) check valve means controlling fluid flow through said outlet means, said check valve means preventing fluid flow into said enclosure through said outlet means and permitting fluid flow from said enclosure through said outlet means only when there is a predetermined pressure differential across said check valve means;

(e) first conduit means for conducting fuel from said first fuel line to said fuel inlet means; and (f) second conduit means for conducting fluid from said check valve into said conduit means connected between said intake manifold downstream from said throttle valve and said PCV valve.

2. A fuel distribution system as defined in claim 1 wherein said float means is adapted to insert said needle valve in said valve seat and obstruct the flow of fuel therethrough when the amount of liquid fuel in said enclosure exceeds approximately three ounces.

3. A fuel distribution system as defined in claim 1 wherein said check valve remains closed until the pressure in said enclosure exceeds the pressure in said second conduit means by at least 1.5 inches of mercury.

4. A fuel distribution system as defined in claim 1 including a normally open check valve permitting fluid flow into said enclosure through said air inlet means and preventing fluid flow from said enclosure through said air inlet means.

5. A fuel distribution system as defined in claim 1 wherein said fuel inlet means, said air inlet means, and said outlet means are sized to maintain a negative pressure in said enclosure of approximately two and one-half inches of mercury when the pressure in said intake manifold is approximately 18 to 20 inches of mercury.

6. A fuel distribution system as defined in claim 1 wherein the orifice in said valve seat is approximately 0.030 inch in diameter, said air inlet means is an orifice approximately 0.125 inch in diameter, and flow through said check valve means is controlled by an orifice in the inlet thereof approximately 0.250 inch in diameter.

7. A fuel distribution system as defined in claim 6 wherein said valve seat is a 45° conical opening flaring outwardly on the bottom side thereof, said needle is an upwardly projecting pointed conical shaft with a 30° from vertical slope on the sides thereof, and the vertical travel of said float between the open and closed positions of said needle valve is restricted to approximately 0.030 inch.

* * * * *

UNITED STATES PATENT OFFICE

CERTIFICATE OF CORRECTION

Patent No. 4,175,525 Dated November 27, 1979

Inventor(s) Edward E. Johnson

It is certified that error appears in the above-identified patent and that said Letters Patent are hereby corrected as shown below:

In Column 2, line 40, "(PVC)" should read ---(PCV)---

In Column 2, line 41, "PVC" should read ---PCV---

In Column 3, line 45, "with" should read ---within---

In Column 6, line 63, "dimension" should read ---dimensions---

In Column 7, line 43, "with" should read ---when---

In Column 8, line 22, "the" should read ---again---

UNITED STATES PATENT OFFICE

CERTIFICATE OF CORRECTION

Patent No. 4,175,525 Dated November 27, 1979

Inventor(s) Edward E. Johnson

It is certified that error appears in the above-identified patent and that said Letters Patent are hereby corrected as shown below:

In Table I, the third line in the column entitled "Engine", "4 cycle" should read ---4 cyl.---

In Table I, the seventh line in the column entitled "Engine", "6 cy. 250" should read ---6 cyl. 250---

In Table I, the last line in the column entitled "MPG", "*" should read ---**---

Signed and Sealed this

*Twenty-fifth* Day of *March 1980*

[SEAL]

*Attest:*

SIDNEY A. DIAMOND

*Attesting Officer* *Commissioner of Patents and Trademarks*